United States Patent [19]

Carlson

[11] 4,423,046
[45] Dec. 27, 1983

[54] ANTIBACTERIAL AND ANTIPROTOZOAL 1-METHYL-5-NITRO-2-(2-PHENYLVINYL-)IMIDAZOLES

[75] Inventor: John A. Carlson, Nassau, N.Y.
[73] Assignee: Sterling Drug Inc., New York, N.Y.
[21] Appl. No.: 365,482
[22] Filed: Apr. 5, 1982
[51] Int. Cl.$^3$ .................... A01N 43/50; A01N 43/84; C07D 233/94; C07D 413/10
[52] U.S. Cl. ................. 424/248.4; 424/272; 424/273 R; 542/405
[58] Field of Search ........... 544/139; 542/405; 548/338, 235; 42.1/273 R, 272, 248.4

[56] References Cited
U.S. PATENT DOCUMENTS

| | | | |
|---|---|---|---|
| 3,391,156 | 7/1968 | Beaman et al. | 548/338 |
| 3,487,087 | 12/1969 | Sarett et al. | 424/273 R |
| 3,549,626 | 12/1970 | Miller et al. | 542/405 |
| 3,658,797 | 4/1972 | Ross et al. | 542/405 |

FOREIGN PATENT DOCUMENTS 2035905 2/1972 Fed. Rep. of Germany .

OTHER PUBLICATIONS

Ross et al., J. Med. Chem. 15, 1035–1040 (1972).
Ross et al., J. Med. Chem. 16, 347 (1973).

Primary Examiner—Richard Raymond
Attorney, Agent, or Firm—William G. Webb; B. Woodrow Wyatt

[57] ABSTRACT

1-Methyl-5-nitro-2-(2-phenylvinyl)imidazoles, having useful antibacterial and antiprotozoal activities, are prepared by chemical transformations of the cyano functional group in a corresponding 1-methyl-5-nitro-2-[2-(cyanophenyl)vinyl]imidazole.

10 Claims, No Drawings

ANTIBACTERIAL AND ANTIPROTOZOAL 1-METHYL-5-NITRO-2-(2-PHENYLVINYL-)IMIDAZOLES

BACKGROUND OF THE INVENTION (a) Field of the Invention

This invention relates to 1-methyl-5-nitro-2-(2-phenylvinyl)imidazoles, useful as antibacterial and antiprotozoal agents.

(b) Description of the Prior Art

German patent application No. 2,035,905 discloses, inter alia, 1-(1-methyl-5-nitro-2-imidazolyl)-2-(4-cyanophenyl)ethylene and 1-(1-methyl-5-nitro-2-imidazolyl)-2-(4-carboxyphenyl)ethylene. Although the patent disclosure speaks of various known 1,2-disubstituted-5-nitro-imidazoles having bactericidal and fungicidal activities, no utility for the compounds that are the subject of the application is given.

Ross et al., J. Med. Chem. 15, 1035-1040 (1972) disclose a series of "2-styryl-5-nitroimidazoles" substituted on the 1-position by ethyl, vinyl or 2-hydroxyethyl, and wherein the phenyl ring of the styryl moiety is either unsubstituted or is substituted by lower-alkyl, chlorine, cycloalkyl, phenyl or methoxy. The compounds were studied for their potential anti-parasitic properties, and the authors concluded that the structural features essential for the desired activity were: "(1) The benzene ring should be substituted by a small 4-alkyl group which itself should carry a hydrogen atom on the α-carbon atom. (2) The linkage between the nitroimidazole and the aryl function should be olefinic. (3) The nitroimidazole should carry an N-vinyl substituent."

In a further publication of their research on 5-nitro-1-vinyl-2-styrylimidazoles at J. Med. Chem. 16, 347 (1973), the same authors reported the preparation of additional species of the class wherein the phenyl ring of the styryl moiety is substituted by various "unsaturated" functional groups, such as formyl, carboxy, cyano, carboxylic ester or carbamyl groups. The 1-vinyl substituted compounds, which became the primary focus of the Ross et al. work, have the disadvantage that the vinyl group cannot be directly introduced into the molecule but must be generated by chemical manipulations of other groups.

Sarett U.S. Pat. No. 3,487,087 discloses compounds having the formula:

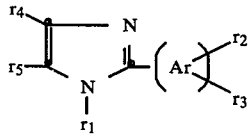

"where Ar is aryl; $r_1$ is . . . lower-alkyl . . . $r_2$ is hydrogen, . . . $r_3$ represents hydrogen . . . carboxy, . . . cyano, carboxamido, . . . amidino, . . . lower-alkoxycarbonyl; and $r_4$ and $r_5$ are hydrogen or nitro, provided that one and only one of $r_4$ and $r_5$ is nitro."

The compounds are stated to be useful as antiprotozoals, particularly against histomoniasis and trichomoniasis.

Miller U.S. Pat. No. 3,549,626 discloses compounds asserted to be "useful as intermediates in the preparation of substituted imidazoles having anti-trichomonal, anti-histomonal, anti-bacterial and anti-parasitic activity" having the formula:

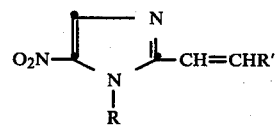

"wherein R is lower-alkyl and R' is phenyl, halophenyl, lower alkylphenyl and lower alkoxyphenyl."

SUMMARY OF THE INVENTION

In a composition of matter aspect, the invention relates to certain 1-methyl-5-nitro-2-(2-phenylvinyl)imidazoles, which are generally useful as antibacterial agents, some of which are also useful as antiprotozoal agents.

DETAILED DESCRIPTION INCLUSIVE OF THE PREFERRED EMBODIMENTS

More specifically, this invention relates to 1-methyl-5-nitro-2-(2-phenylvinyl)imidazoles, which are useful as antibacterial and antiprotozoal agents, having the formula:

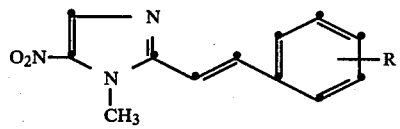

where R is carbamyl ($CONH_2$), lower-alkoxyiminocarbonyl [$—C(=NH)OR'$, where R' is lower-alkyl], amidinyl [$—C(=NH)—NH_2$], 2-oxazolyl or 2-oxazinyl.

As used herein, the terms lower-alkyl and lower-alkoxy mean saturated, monovalent, aliphatic radicals, including branched chain radicals, of from one to six carbon atoms and thus include such groups, for example, as methyl, ethyl, propyl, isopropyl, butyl, hexyl, methoxy, ethoxy, propoxy, isopropoxy, butoxy, hexyloxy, and the like.

The compounds of formula I where R is carbamyl are prepared by treating a corresponding compound where R is cyano with concentrated sulfuric acid and then decomposing the reaction mixture with water.

The compounds of formula I where R is lower-alkoxyiminocarbonyl are prepared by reacting a corresponding compound where R is cyano with a lower-alkanol in the presence of an anhydrous mineral acid. The reaction is preferably carried out by suspending the starting material in the lower-alkanol at a temperature around 0°-5° C. and treating the suspension, with stirring, with a stream of anhydrous hydrogen chloride gas.

The compounds of formula I where R is amidinyl are prepared by reacting a corresponding compound where R is lower-alkoxyiminocarbonyl with a source of ammonia. The reaction is preferably carried out by refluxing a solution of the starting material in a lower-alkanol, for example methanol, ethanol or isopropanol, in the presence of an ammonium halide, for example ammonium chloride.

The compounds of formula I where R is 2-oxazolyl or 2-oxavinyl are prepared by reacting a corresponding compound where R is lower-alkoxyiminocarbonyl with, respectively, 2-aminoethanol or 3-aminopropanol. The reaction is preferably carried out by heating the reactants at reflux temperature in an organic solvent inert under the conditions of the reaction, for example dioxane, benzene, toluene or dibutyl ether.

The compounds of the invention can be isolated and used either in free base form or in the form of their acid-addition salts. The free bases are converted to the acid-addition salt form by interaction of the base with an acid. In like manner, the free base can be regenerated from the acid-addition salt form in the conventional manner, that is by treating the salts with cold, weak aqueous bases, for example alkali metal carbonates and alkali metal bicarbonates. The bases thus regenerated can then be interacted with the same or a different acid to give back the same or a different acid-addition salt. Thus the novel bases and all of their acid-addition salts are readily interconvertible.

It will thus be appreciated that formula I not only represents the structural configuration of the bases of formula I but is also representative of the structural entity which is common to the compounds of formula I, whether in the form of the free bases or in the form of the acid-addition salts of the bases. It has been found that, by virtue of this common structural entity, the bases and the acid-addition salts of the compounds of formula I have inherent biological activities of a type to be more fully described hereinbelow. These inherent biological activities can be enjoyed in useful form for pharmaceutical purposes by employing the free bases themselves or the acid-addition salts formed from pharmaceutically-acceptable acids, that is acids whose anions are innocuous to the animal organism in effective doses of the salts so that beneficial properties inherent in the common structural entity represented by the free bases are not vitiated by side effects ascribable to the anions.

In utilizing the biological activities of the salts of the invention, it is preferred, of course, to use pharmaceutically acceptable salts. Although water-insolubility, high toxicity or lack of crystalline character may make some particular salt species unsuitable or less desirable for use as such in a given pharmaceutical application, the water-insoluble or toxic salts can be converted to the corresponding pharmaceutically-acceptable bases by decomposition of the salts with aqueous base as explained above, or alternatively they can be converted to any desired pharmaceutically-acceptable acid-addition salt by double decomposition reactions involving the anion, for example by ion-exchange procedures.

Moreover, apart from their usefulness in pharmaceutical applications, the salts are useful as characterizing or identifying derivatives of the free bases or in isolation or purification procedures. Like all of the acid-addition salts, such characterizing or purification salt derivatives can, if desired, be used to regenerate the pharmaceutically-acceptable free bases by reaction of the salts with aqueous base, or alternatively they can be converted to a pharmaceutically-acceptable acid-addition salt by, for example, ion-exchange procedures.

It will be appreciated from the foregoing that all of the acid-addition salts of the new bases are useful and valuable compounds, regardless of considerations of solubility, toxicity, physical form and the like, and are accordingly within the purview of the instant invention.

The novel feature of the compounds of the invention, then, resides in the concept of the bases and cationic forms of the new 1-methyl-5-nitro-2-(2-phenylvinyl)imidazoles and not in any particular acid moiety or acid anion associated with the salt forms of the compounds; rather, the acid moieties or anions which can be associated with the salt forms are in themselves neither novel nor critical and therefore can be any acid anion or acid-like substance capable of salt formation with the bases. In fact, in aqueous solutions the base form or water-soluble acid-addition salt form of the compounds of the invention both possess a common protonated cation or ammonium ion.

Thus appropriate acid-addition salts are those derived from such diverse acids as formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylenedicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic acid, isethionic acid, benzenesulfonic acid, p-toluenesulfonic acid, benzenesulfinic acid, butylarsonic acid, diethylphosphonic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride, and the like.

The acid-addition salts are prepared by reacting the free base and the acid in an organic solvent and isolating the salts directly or by concentration of the solution.

In standard biological test procedures, the compounds of formula I have been found to possess useful antibacterial and antiprotozoal activities. Thus in a standard serial dilution antibacterial test, described in Schulenberg U.S. Pat. No. 3,728,388, they have been found to have antibacterial activity and are thus useful as antibacterial agents.

Moreover, in standard antiprotozoal tests described in Carabateas U.S. Pat. No. 3,382,256, Bailey U.S. Pat. No. 3,997,542 and Alexander U.S. Pat. No. 4,105,766, certain species of the compounds of formula I have been found to be active against *Entamoeba criceti, Trypanosoma brucei, Trichomonas vaginalis* and *Trichomonas gallinae.*

When intended for use as antibacterial agents, the compounds can be formulated by preparing a dilute solution in an aqueous medium or in a solution containing a surfactant. Alternatively, they can be dissolved in an organic medium in which the compounds are soluble and applied to a surface to be disinfected by spraying, swabbing, immersion and the like. The compounds can also be formulated as ointments or creams by incorporating them in conventional ointment or cream bases, for example alkyl polyether alcohols, cetyl alcohol, stearyl alcohol and the like, or as jellies by incorporating them in conventional jelly bases, such as glycerol and tragacanth. They can also be formulated for use as aerosol sprays or foams.

When intended for use as antiprotozoal agents, the compounds can be formulated by incorporation in unit dosage form as tablets or capsules for oral administration either alone or in combination with suitable adjuvants, such as calcium carbonate, starch, lactose, sodium bicarbonate, sodium lauryl sulfate, sugar, dextrose, mannitol, cellulose, gum acacia and the like. Alternatively, they can be formulated for oral administration in aqueous alcohol, glycol or oil solutions or oil-water emulsions in the same manner as conventional medicinal substances are prepared. They can also be formulated for oral use in foodstuffs or admixed with foodstuffs for veterinary use.

The structures of the compounds of the invention were established by their mode of synthesis, by elementary analyses and by their ultraviolet, infrared and nuclear magnetic resonance spectra. The course of reactions, and the homogeneity of the products, were ascertained by thin layer chromatography.

The manner and process of making and using the compounds of the invention, and the best mode contemplated for carrying out the invention, will now be described so as to enable any person skilled in the art to which it pertains to make and use the same. The melting points are uncorrected.

PREPARATION OF THE STARTING MATERIALS

PREPARATION 1A

To a hot solution of 25 g. (0.21 mole) of 1,2-dimethyl-5-nitroimidazole and 25 g. (0.19 mole) of 4-cyanobenzaldehyde in 100 ml. of ethanol was added a solution of 38 g. (0.34 mole) of potassium t-butoxide in 150 ml. of hot ethanol. The solution was stirred for two minutes, cooled in an ice bath, and the solid which separated was collected by filtration, washed with ethanol and recrystallized from ethanol to give 24 g. of 1-methyl-5-nitro-2-[2-(4-cyanophenyl)vinyl]imidazole, m.p. 287°–288° C.

Preparation 1B

Following a procedure similar to that described in Preparation 1A above, 1-methyl-5-nitro-2-[2-(3-cyanophenyl)vinyl]imidazole, m.p. 233°–235° C. (21.5 g. from ethanol) was prepared by reaction of 25 g. (0.21 mole) of 1,2-dimethyl-5-nitroimidazole with 25 g. (0.19 mole) of 3-cyanobenzaldehyde in ethanol in the presence of 30 g. (0.27 mole) of potassium t-butoxide.

PREPARATION OF THE FINAL PRODUCTS

Example 1A

To 5 ml. of cold 90% sulfuric acid was added 1 g. (0.004 mole) of 1-methyl-5-nitro-2-[2-(3-cyanophenyl)vinyl]imidazole, and the resulting solution was warmed on a steam bath for five minutes and then poured into ice water. The solid which separated was collected by filtration, washed with water, dried and recrystallized from ethanol to give 1-methyl-5-nitro-2-[2-(3-carbamylphenyl)vinyl]imidazole, m.p. 254°–256° C.

EXAMPLE 1B

Following a procedure similar to that described in Example 1A above, 1-methyl-5-nitro-2-[2-(4-carbamylphenyl)vinyl]imidazole, m.p. 285°–289° C. (10 g., from ethanol) was prepared by treatment of about 0.19 mole of 1-methyl-5-nitro-2-[2-(4-cyanophenyl)vinyl]imidazole with 100 ml. of cold 90% sulfuric acid followed by quenching the reaction mixture in ice water.

Example 2A

Into a stirred suspension of 26.2 g. (0.103 mole) of 1-methyl-5-nitro-2-[2-(4-cyanophenyl)vinyl]imidazole in 1 liter of ethanol was passed a rapid stream of anhydrous hydrogen chloride while cooling the reaction mixture in an ice bath. Saturation of the mixture with hydrogen chloride was continued at 30° C. for one hour, and then the reaction mixture was cooled for about forty-eight hours. The resulting solution was concentrated to a small volume in vacuo, diluted with aqueous sodium carbonate solution, and the solid which separated was collected by filtration and recrystallized from ethanol to give 13 g. of 1-methyl-5-nitro-2-[2-(4-ethoxyiminocarbonylphenyl)vinyl]imidazole, m.p. 178°–179° C.

Example 2B

Following a procedure similar to that described in Example 2A above, 1-methyl-5-nitro-2-[2-(4-butoxyiminocarbonylphenyl)vinyl]imidazole, m.p. 145° C. (4 g., from acetonitrile) was prepared by treatment of 10 g. (0.039 mole) of 1-methyl-5-nitro-2-[2-(4-cyanophenyl)vinyl]imidazole in n-butanol with anhydrous hydrogen chloride.

Example 3

A stirred suspension of 15 g. (0.059 mole) of 1-methyl-5-nitro-2-[2-(4-cyanophenyl)vinyl]imidazole in 500 ml. of ethanol was treated with a stream of anhydrous hydrogen chloride while maintaining the reaction temperature at less than 30° C. The reaction mixture was stored at about 0° C. for forty-eight hours, then filtered and the filtrate evaporated to dryness in vacuo. The residue was washed with diethyl ether and then suspended in 300 ml. of methanol. The suspension was treated with 5 g. of ammonium chloride, and the resulting mixture was heated under reflux for about twelve hours and then cooled and filtered. The solid was dissolved in 10% hydrogen chloride, the solution filtered, and the filtrate was basified with 10% aqueous sodium carbonate solution. The solid which separated was collected by filtration, washed with water, dried and recrystallized from ethanol to give 8.5 g. of 1-methyl-5-nitro-2-[2-(4-amidinylphenyl)vinyl]imidazole, m.p. 233°–235° C.

Example 4A

To a solution of 5.0 g. (0.017 mole) of 1-methyl-5-nitro-2-[2-(4-ethoxyiminocarbonylphenyl)vinyl]imidazole in 50 ml. of dioxane was added 5 ml. of 2-aminoethanol, and the solution was heated under reflux under a nitrogen atmosphere for eighteen hours. The mixture was then cooled, filtered and the filtrate evaporated to dryness in vacuo. The residue was dissolved in 15 ml. of ethanol, the solution was diluted with 100 ml. of water, and the solid that separated was collected and recrystallized from acetonitrile to give 2.5 g. of 1-methyl-5-nitro-2-{2-[4-(2-oxazolyl)phenyl]vinyl}imidazole, m.p. 238° C.

Example 4B

Following a procedure similar to that described in Example 4A above, 1-methyl-5-nitro-2-{2-[4-(2-oxazinyl)phenyl]vinyl}imidazole, m.p. 222° C. (2.2 g., from acetonitrile) was prepared by reaction of 8 g. (0.027 mole) of 1-methyl-5-nitro-2-[2-(4-ethoxyiminocarbonylphenyl)vinyl]imidazole with 8 ml. of 3-aminopropanol.

BIOLOGICAL TEST RESULTS

The compounds of the invention were tested in in vitro antibacterial and antifungal tests and found to have general antibacterial activity against a variety of bacterial micro-organisms. Data so-obtained, expressed as the minimum inhibitory (bactericidal) concentration (MIC) (in micrograms/milliliter), are given in the table below, where the letters A, B, C, D, E, F and G represent, respectively, the bacterial organisms *S. aureus Smith, E. coli vogel, K. pneumoniae* 39645, *P. mirabilis* MGH-1, *Ps. aeruginosa* MGH-2, *S. pyogenes* C203 and *S. mutans* OMZ61, and the letters H, I and J represent the fungal micro-organisms *C. albicans* 10231, *As. niger* 16404 and *T. mentagrophytes* 9129, respectively.

| Example | A | B | C | D | E | F | G | H | I | J |
|---------|------|------|------|------|------|------|-----|------|------|------|
| 1A | 500 | >125 | >125 | >125 | >125 | — | — | >125 | >125 | >125 |
| 1B | 62.5 | >250 | 31.3 | >125 | >125 | — | 1.0 | >125 | >125 | >125 |
| 2A | 125 | >250 | >125 | >125 | 125 | — | 7.8 | >125 | >125 | >125 |
| 2B | >125 | >62.5 | >62.5 | >125 | 62.5 | 1.95 | 3.9 | >125 | >125 | >250 |
| 3 | <7.8 | >125 | <7.8 | 125 | 125 | — | 3.9 | >125 | >125 | >125 |
| 4A | 62.5 | >62.5 | 62.5 | 125 | 62.5 | 3.13 | — | >62.5 | >62.5 | >62.5 |
| 4B | 12.5 | >125 | 125 | >250 | 125 | 31.3 | — | >125 | >125 | >125 |

Certain species of the invention have also been found to be active against various internal parasites. For example, the species of Examples 1A, 1B and 2A have all been found active, when administered orally, against *Entamoeba criceti*. In addition, the species of Example 2A was found active, when administered orally, against *Trypanosoma brucei* and certain species of Trichomonas, for example *T. gallinae* and *T. vaginalis*. The species of Example 3 has been found to be active, when administered either orally or intraperitoneally, against *Trypanosoma brucei*. The species of Examples 1A and 1B were found to be inactive as trichomonacidal or trypanosomacidal agents, and the species of Example 3 was found to be inactive as an amoebacidal or trichomonacidal agent.

I claim:
1. A member of the group consisting of (A) compounds having the formula:

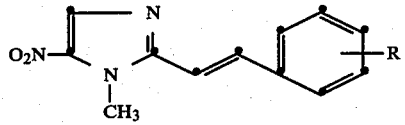

where R is lower-alkoxyiminocarbonyl, amidinyl, 2-oxazolyl or 2-oxazinyl; and (B) acid-addition salts thereof.

2. A compound according to claim 1 where R is lower-alkoxyiminocarbonyl.

3. A compound according to claim 1 where R is amidinyl.

4. A compound according to claim 1 where R is 2-oxazolyl or 2-oxazinyl.

5. 1-Methyl-5-nitro-2-[2-(4-ethoxyiminocarbonylphenyl)vinyl]imidazole according to claim 2.

6. 1-Methyl-5-nitro-2-[2-(4-butoxyiminocarbonylphenyl)vinyl]imidazole according to claim 2.

7. 1-Methyl-5-nitro-2-[2-(4-amidinylphenyl)vinyl]imidazole according to claim 3.

8. 1-Methyl-5-nitro-2-{2-[4-(2-oxazolyl)phenyl]vinyl}imidazole according to claim 4.

9. 1-Methyl-5-nitro-2-{2-[4-(2-oxazinyl)phenyl]vinyl}imidazole according to claim 4.

10. A method of killing bacteria on surfaces or in media containing such bacteria which comprises treating said surfaces or such media with a composition containing, as the active ingredient therein, a bactericidally effective amount of a compound having the formula:

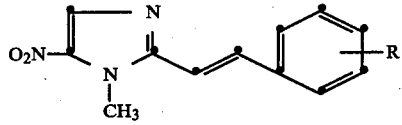

where R is lower-alkoxyiminocarbamyl, amidinyl, 2-oxazolyl or 2-oxazinyl.

* * * * *